United States Patent [19]

Kojima et al.

[11] Patent Number: 4,996,357

[45] Date of Patent: Feb. 26, 1991

[54] PROCESS FOR PREPARING ACETIC ACID

[75] Inventors: Hidetaka Kojima; Takaaki Fujiwa, both of Himeji, Japan

[73] Assignee: Daicel Chemical Industries, Ltd., Osaka, Japan

[21] Appl. No.: 717,629

[22] Filed: Mar. 29, 1985

[30] Foreign Application Priority Data

Apr. 5, 1984 [JP] Japan ................................. 59-68212

[51] Int. Cl.$^5$ ................... C07C 51/12; C07C 51/353; C07C 53/08
[52] U.S. Cl. .................................. 562/607; 560/234; 560/265
[58] Field of Search ................. 562/607, 517; 560/234

[56] References Cited

U.S. PATENT DOCUMENTS 4,613,693  9/1986  Ray ..................................... 562/517

FOREIGN PATENT DOCUMENTS

| 45637 | 12/1982 | European Pat. Off. ............ 562/607 |
| 109212 | 5/1984 | European Pat. Off. ............ 562/517 |
| 1072979 | 1/1960 | Fed. Rep. of Germany ...... 562/606 |
| 3236351 | 4/1984 | Fed. Rep. of Germany ...... 562/607 |
| 1286224 | 8/1972 | United Kingdom ................ 562/517 |

*Primary Examiner*—Vivian Garner
*Attorney, Agent, or Firm*—Flynn, Thiel, Boutell & Tanis

[57] ABSTRACT

Acetic acid is advantageously prepared from a starting material having a formic acid moiety and a methyl ester moiety by heating said starting material in the presence of (1) carbon monoxide, (2) at least one of (2-a) a metal accelerator selected from beryllium, a metal belonging to the group IIIA, IVB, VB, VIB or IIA of the Periodic Table, a lanthanide metal and an actinide metal and (2-b) an onium compound or a precursor for the onium compound, (3) a rhodium catalyst and (4) an iodine compound.

13 Claims, No Drawings

PROCESS FOR PREPARING ACETIC ACID

The present invention relates to a process for preparing acetic acid from a raw material having a formic acid moiety and a methyl ester moiety in the presence of a metal accelerator or an onium compound, a rhodium catalyst and an iodine compound.

Methyl formate or formic acid can be prepared from various raw materials such as carbon monoxide or methanol. It is industrially advantageous to prepare acetic acid from such abundant resources via liquid compounds convenient for transport.

It is known as described in British Patent No. 628161 that methyl formate is heated in a pressurized carbon monoxide atmosphere to give acetic acid. Further, it is also known that the reaction proceeds in the presence of a rhodium catalyst even at a lower temperature to obtain acetic acid selectively at a high purity at a high yield (see Japanese Patent Publication No. 3513/1974 and U.S. Pat. No. 4,194,056).

However, rhodium is expensive, so that it is advantageously used only when the catalytic activity is high and the decrease in the activity is very small. Accordingly, processes wherein other metals can be used as a catalyst have been studied (Japanese Patent Laid-Open Nos. 33745/1981, 83439/1981 and 203028/1982).

It is an object of the present invention to provide an improved process by which the conversion rate of methyl formate into acetic acid in the presence of a rhodium catalyst is enhanced and a high productivity can be achieved even if a small amount of rhodium is used. Additionally, the present invention enables the use of a mixture of formic acid and a methyl ester of a carboxylic acid other than formic acid, such as acetic acid, as raw materials for the preparation of acetic acid as well as methyl formate.

The inventors of the present invention have studied various acceleration processes, and have found that the catalytic activity can be remarkably enhanced and the reaction can proceed even at a lower temperature than that of the prior art, by using at least a metal accelerator or an onium compound and carrying out the reaction in a carbon monoxide atmosphere. The present invention has been accomplished on the basis of this finding.

(SUMMARY OF THE INVENTION)

The invention process is characterized by heating the starting material in the presence of (1) carbon monoxide, (2) at least one of (2-a) a metal accelerator selected from beryllium, a metal belonging to the group IIIA, IVB, VB, VIB or IIA of the Periodic Table, a lanthanide metal and an actinide metal and (2-b) an onium compound or a precursor of the onium compound, (3) a rhodium catalyst and (4) an iodine compound.

The onium compound (2-b) is an organic compound of pentavalent nitrogen or phosphorus such as ammonium, pyridinium and phosphonium. In addition, it may include a precursor of the pentavalent organic compound, having a trivalent nitrogen or phosphorus, which is convertable to the pentavalent compound in the reaction step of the invention.

The invention provides preferable embodiments of the component (2), that is, (2-a) and/or (2-b), as follows: a metal accelerator selected from the group consisting of a metal belonging to the group IIIA, IVB or VIB and beryllium, a metal accelerator selected from the group consisting of aluminum, zirconium, titanium and beryllium, a metal accelerator of aluminum, a metal accelerator of a metal belonging to the group IVB, both an onium compound or a precursor thereof and a metal accelerator of a metal belonging to the group IVB, both an onium compound or a precursor thereof and a metal accelerator of chromium, a metal accelerator and further hydrogen gas, a metal accelerator selected from aluminum, zirconium, titanium and beryllium and further hydrogen gas and a metal accelerator of beryllium and further hydrogen gas.

(METAL ACCELERATOR)

The metal accelerator to be used in the invention is defined above. A suitable example thereof is Be, Ti, Zr, Hf, V, Nb, Ta, Cr, Mo, W, Zn, Al, La, Ce and Th. Be, Ti, Zr, V, Cr, Zn and Al are preferably used. Only one metal or a combination of two or more metals may be used. Some of the combinations exhibit a composite effect.

The metal accelerators may be generally used in the form which can generate a metal ion when dissolved in a reaction mixture, for example, in the form of metal, halide, oxide, hydroxide, nitrate, carboxylate, carbonate, alkylalcoholate, acetylacetonate or metal carbonyl compound. Slightly soluble or insoluble compounds, stable oxide, salts of oxyacid or compounds which are poisonous to the catalyst are not preferred.

The amount of a metal accelerator to be added is 5 to 700 mmol/l of the reaction mixture, preferably 10 to 500 mmol/l.

(ONIUM COMPOUND)

The onium compound of the invention is an organic compound having a trivalent or pentavalent nitrogen or phosphorus atom and may be used by itself or together with the metal accelerator. In the invention process, the organic compound having a trivalent nitrogen or phosphorus atom reacts with methyl iodide to form an ammonium, pyridinium or phosphonium compound.

An example of a precursor of the onium compound is a tertiary phosphine such as tributylphosphine and triphenylphosphine, a pyridine base, an amine and an imide. The accelerators as described in the prior art, for example, Japanese Patent Laid-Open No. 115403/1976, pp. 6 and 7 can be also used. Examples of the organic compound containing a pentavalent nitrogen or phosphorus atom include accelerators as described in the prior art, for example, Japanese Patent Laid-Open No. 57733/1981, p. 3.

The organic compounds containing a nitrogen or phosphorus atom can be used in the form in which the compounds are coordinated to rhodium as described below.

An amount of the onium compound is preferably 4 to 50 mol, more preferably 5 to 20 mol, per one mol of rhodium.

(RHODIUM CATALYST)

A rhodium catalyst can be added to the reaction system in the form of, for example, rhodium halide such as $RhCl_3 \cdot 3H_2O$ or $RhI_3$; rhodium carbonyl compounds such as $[Rh(CO)_2Cl]_2$, $Rh(CO)_2(C_5H_7O_2)$, $Rh_4(CO)_{12}$ or $Rh_6(CO)_{16}$; phosphine-coordinated rhodium compounds such as $RhCl[P(C_6H_5)_3]_3$, $RhCl(CO)[P(C_6H_5)_3]_2$ or $RhH(CO)[P(C_6H_5)_3]_3$ or amine- or pyridine-coordinated rhodium compounds such as $[Rh(C_2H_8N_2)_3]Cl_3 \cdot 3H_2O$ or $[Rh(C_5H_5N)_4Cl_2]Cl \cdot 5H_2O$. Phosphine- or nitrogen compound-coordinated rhodium compounds sometimes exhibit a higher accelerating effect than other rhodium compounds, depending upon the kind of metal accelerator. But, the phosphine or nitrogen compound need not coordinate to rhodium and may be added separately. Alternatively, it may be added as an onium compound such as ammonium or phosphonium obtained by the reaction with alkyl halide such as methyl iodide. The method comprising adding rhodium and an onium compound separately has some advantages in that rhodium chloride or rhodium iodide which is relatively inexpensive and easily available and can be easily handled is used in the reaction and that the amount of the phosphine or nitrogen compound to be added can be selected arbitrarily.

The amount of rhodium to be added to the reaction mixture is generally 0.1 to 50 mmol/l, preferably 1 to 30 mmol/l.

(IODINE COMPOUND)

Examples of the iodine compounds to be used include iodine, alkyl iodide such as methyl iodide and hydrogen iodide. The iodine compound may be added in the form of an iodide of the metal used as an accelerator. The amount of the iodine compound to be used is generally 0.1 to 10 mol/l, preferably 0.5 to 5 mol/l.

(RAW MATERIAL)

The raw material for acetic acid preparation to be used in this invention has a formic acid moiety and a methyl ester moiety. The term "formic acid moiety" refers to an HCOO-group contained in formic acid or a formate. A formic acid moiety and a methyl ester moiety may be present in one molecule, or may be separately present in different molecules from each other. When a formic acid moiety and a methyl ester moiety are present in one molecule, the raw material is methyl formate, while when they are separately present in different molecules respectively, it is a mixture of formic acid and methyl carboxylate such as methyl acetate or methyl propionate or a mixture of an alkyl formate such as ethyl formate and a methyl carboxylate. A mixture of formic acid and methyl acetate is preferred from the standpoint of the simplification of the composition of the reaction system.

(CARBON MONOXIDE)

Though carbon monoxide is not consumed during the reaction, it is required to activate a rhodium catalyst and maintain the catalytic activity. The reaction is carried out in a carbon monoxide atmosphere of at least 5 kg/cm$^2$, preferably 10 to 50 kg/cm$^2$ to obtain acetic acid in a high yield. The carbon monoxide to be used need not be pure and may contain methane, carbon dioxide, nitrogen, hydrogen or the like, as far as it can give the above partial pressure of carbon monoxide.

(REACTION CONDITION)

The reaction is carried out in a liquid phase. The raw materials act as a liquid medium, so that no additional solvent need be added. Practically, acetic acid which is a reaction product is added.

Alternatively carboxylic acids such as propionic or butyric acid may be used. In some cases, amide, nitrile, ketone, boric acid or the like may be used to enhance the solubility of a metal accelerator.

The reaction temperature is 100° to 250° C., preferably 140° to 200° C.

(TREATMENT OF THE CATALYST WITH HYDROGEN)

If necessary, particularly, when the rhodium catalyst is added as a trivalent rhodium compound or when it is used repeatedly, it is preferred that the rhodium catalyst is treated with hydrogen. By the treatment with hydrogen, the rhodium catalyst can exhibit a high activity and the high catalytic activity can be maintained when used repeatedly.

The treatment of the catalyst with hydrogen may be carried out before feeding to a reactor. Alternatively, it may be carried out in situ using hydrogen present to together with carbon monoxide in a reactor.

(EFFECT OF THE INVENTION)

According to the present invention, the rhodium catalyst exhibits a high catalytic activity, so that acetic acid can be advantageously prepared from liquid raw materials convenient for transport, such as methyl formate or a mixture of formic acid and methyl acetate.

Examples of the present invention and Examples for illustrating the effects of the present invention will be described. In these Examples, the reaction was carried out in an autoclave by a batchwise method, and the pressures described are the ones at an ordinary temperature and at charging.

The invention process will be illustrated below in reference to working examples thereof. Examples 1 to 4, 6 and 10 each show a case where a metal accelerator of aluminum was used in the form of metal powder or a compound thereof and an acetylation rate was effectively accelerated. Examples 13, 15 and 16 are each a case where a metal accelerator of a metal of group IVB, such as zirconium and titanium, was used. A process using the metal accelerator of group IVB was improved by a combination with an onium compound, as seen in Examples 16 and 9. This applied to a case where a metal accelerator of chromium was used. Examples 11 to 16 each show that use of hydrogen gas in combination with a metal accelerator such as aluminum, titanium, zirconium and beryllium much improved the process. Especially a combination of hydrogen gas and beryllium was advantageous. Hydrogen gas is practically introduced into the reaction system at a partial pressure thereof of 0.1 to 50, preferably 1 to 20, kg per cm$^2$.

An amount of acetic acid or methyl acetate in the reaction mixture was determined by gas chromatography. The yields of acetic acid and methyl acetate and the acetylation rate were calculated according to the following formula:

Yield of acetic acid (%) =

$$\frac{\text{moles of generated acetic acid}}{\text{moles of charged methyl formate}} \times 100$$

Yield of methyl acetate (%) =

$$\frac{2 \times \text{moles of generated methyl acetate}}{\text{moles of charged methyl formate}} \times 100$$

Acetylation rate (mol/l · hr) =

$$\frac{\text{generated moles (acetic acid + methyl acetate)}}{\text{(volume of reaction liquid (l))} \times \text{[reaction time (hr)]}}$$

Of course, the process according to the present invention can be carried out continuously by using prior art known in the field. Further, the separation of acetic acid from the reaction mixture and the purification thereof can be easily carried out by those skilled in the art.

EXAMPLE 1

0.34 g of rhodium chloride trihydrate, 4.9 ml of methyl iodide, 0.6 g of aluminum powder, 32 ml of acetic acid and 32 ml of methyl formate were fed into a 300 ml autoclave made of Hastelloy B. The air present in the autoclave was replaced with carbon monoxide, followed by pressurizing to 20 kg/cm. The autoclave was heated to 170° C. and the reaction was carried out at this temperature for one hour. After the completion of the reaction, the autoclave was cooled and the residual pressure was released. The reaction mixture was taken out and gas-chromatographed. The yields of methyl acetate and acetic acid were 0.6 and 98.9%, respectively, while the acetylation rate was 8.0 mol/l hr.

TABLE 1

| Ex. | Yield of methyl acetate (mol %) | Yield of acetic acid (mol %) | Acetylation rate (mol/l.hr) |
| --- | --- | --- | --- |
| 1 | 0.6 | 98.9 | 8.0 |
| 2 | 28.9 | 42.7 | 8.9 |
| 3 | 29.0 | 66.9 | 12.7 |
| 4 | 46.8 | 15.6 | 6.1 |
| 5 | 49.9 | 21.9 | 7.3 |
| 6 | 23.1 | 56.1 | 10.2 |
| 7 | 53.0 | 7.0 | 5.1 |
| 8 | 13.4 | 35.0 | 6.0 |
| 9 | 3.6 | 85.2 | 12.5 |
| 10 | 8.6 | 27.8 | 10.1 |
| 11 | 10.3 | 87.6 | 14.4 |
| 12 | 4.9 | 80.6 | 11.9 |
| 13 | 11.7 | 66.9 | 10.1 |
| 14 | 16.8 | 66.2 | 11.7 |
| 15 | 22.9 | 28.4 | 6.2 |
| 16 | 16.8 | 72.5 | 11.8 |
| 17 | 31.0 | 47.6 | 9.5 |
| 18 | 9.6 | 39.0 | 13.1 |
| 20 | 47.9 | 17.6 | 6.5 |
| 21 |  | 99.1 |  |
| 22 | 16.7 | 47.9 | 4.3 |
| 23 |  | 100 |  |

COMPARATIVE EXAMPLE 1

This Comparative Example shows the case where no aluminum powder was added. The reaction mixture comprised 22.2% of methyl formate, 20.6% of methyl acetate and 35.7% of acetic acid. The amount of acetic acid decreased as compared with the one of the initially charged acetic acid of 44%, while the amount of methyl acetate increased. The acetylation rate was only 1.2 mol/l.hr.

In examples 2 to 20 and Comparative Example 2, the reaction time was 30 minutes in order to clearly indicate the effects of the addition of an accelerator on the results of the reaction. The same conditions as the ones described in Example 1 were used, unless otherwise stated. The results of the reaction are shown in Table 1.

EXAMPLE 2 to 4

Each reaction was carried out at a pressure of carbon monoxide of 30, 20, or 10 kg/cm²G respectively.

EXAMPLES 5 to 8

The following compounds (the amount being represented by mmol) were used as an accelerator instead of the aluminum powder.

Example 5: chromium carbonyl Cr(CO)$_6$ (1.3)
Example 6: aluminum acetate Al(OAc)$_3$ (22)
Example 7: beryllium chloride BeCl$_2$ (22)
Example 8: methyltri-n-butylphosphonium iodide CH$_3$(n- Bu)$_3$PI (21)
Example 9: chromium carbonyl (1.3) and methyltri-n-butylphosphonium iodide (21).

EXAMPLE 10

0.34 g of rhodium chloride trihydrate, 4.9 ml of methyl iodide, 4.5 g of aluminum acetate and 64 ml of methyl formate were fed into the same autoclave as the one used in Example 1, followed by pressurizing by carbon monoxide to 20 kg/cm². The reaction was carried out at 170° C. for 30 minutes.

EXAMPLES 11 to 16

In these Examples, hydrogen (the partial pressure being 10 kg/cm²) was added together with carbon monoxide.

The following compounds were used as an accelerator respectively (the amounts being represented by mmol).

Example 11: aluminum powder (22)
Example 12: aluminum acetate (22)
Example 13: Ti(OCH$_3$)$_4$ (11) and methyltri-n-butylphosphonium iodide (21)
Example 14: beryllium chloride BeCl$_2$ (22)
Example 15: zirconium oxyacetate ZrO(OAc)$_2$ (11)
Example 16: zirconium oxyacetate (11) and methyltri-n-butylphosphonium iodide (11)
Example 18: lithium iodide (22).

In this Example, the partial pressure of carbon monoxide was 40 kg/cm²G.

EXAMPLE 17

The same procedure as the one described in Example 3 was repeated, except that 1.29 mmol of hydridocarbonyltris(triphenylphosphine)rhodium RhH(CO)(PPh$_3$)$_3$ was used instead of rhodium chloride trihydrate and that 6 mmol of zirconium oxyacetate ZrO(OAc)$_2$ was used as an accelerator.

EXAMPLE 18

The same procedure as the one described in Example 12 was repeated, except that 64 ml of methyl formate was used without the addition of acetic acid.

EXAMPLE 19

0.34 g of rhodium chloride trihydrate, 4.9 ml of methyl iodide, 0.6 g of aluminum powder, 27 g (587 mmol) of formic acid and 41 g (553 mmol) of methyl acetate were fed into the same autoclave as the one used in Example 1, followed by pressurizing by carbon monoxide to 20 kg/cm² in the same manner as described in Example 2. The reaction was carried out at 170° C. for 30 minutes. 31 mmol of methyl formate, 72 mmol of methyl acetate and 931 mmol of acetic acid were produced. This means that 81.4 molar % of the amount of the methyl ester moiety contained in the raw material was converted into an acetyl group, corresponding to an acetylation rate of 13.0 mol/l.hr.

COMPARATIVE EXAMPLE 2

The same procedure as the one described in Example 22 was repeated, except that no aluminum powder was used and that the amounts of formic acid and methyl acetate were 41 g (887 mmol) and 32 g (438 mmol), respectively. 150.3 mmol of methyl acetate and 513 mmol of acetic acid were produced. This means that 51.5 molar % of the amount of the methyl ester moiety contained in the raw material was converted into an acetyl group, corresponding to an acetylation rate of 6.3 mol/l.hr.

EXAMPLE 20

0.34 g of rhodium chloride trihydrate, 1.76 g of beryllium chloride and 32 ml of acetic acid were fed into the same autoclave as the one used in Example 1, followed by pressurizing by hydrogen gas containing 16.7% of carbon monoxide to 5 kg/cm$^2$. The autoclave was heated at 130° C. for 30 minutes and cooled. The gas was released and the gas contained in the autoclave was replaced with carbon monoxide. 4.9 ml of methyl iodide and 32 ml of methyl formate were fed into the autoclave, followed by pressurizing by carbon monoxide to 20 kg/cm$^2$ according to the same procedure as the one described in Example 7. Then, the reaction was carried out at 170° C. for 30 minutes.

EXAMPLE 21

The same procedure as the one described in Example 12 was repeated, except that the heating time was 60 minutes. The yield of acetic acid was 99.1%, while no methyl acetate remained.

EXAMPLE 22

The same procedure as the one described in Example 13 was repeated, except that the heating temperature and the heating period were 150° C. and 60 minutes, respectively.

EXAMPLE 23

The same procedure as the one described in Example 13 was repeated, except that the heating period was 60 minutes. All of the added methyl formate was converted into acetic acid within 60 minutes.

COMPARATIVE EXAMPLE 3

The same procedure as the one described in Comparative Example 1 was repeated, except that the autoclave was further pressurized by hydrogen to 10 kg/cm$^2$ in addition to the pressurization by carbon monoxide. The acetylation rate was 1.2 mol/l.hr which is equivalent to the one in Comparative Example 1. That is to say, when no accelerator was present, the effect of hydrogen could not be detected.

The embodiments of the invention in which an exclusive property or privilege is claimed are defined as follows:

1. A process for preparing acetic acid from a starting material selected from the group consisting of (i) methyl formate and (ii) a mixture of formic acid and a methyl carboxylate, which comprises: heating said starting material in the presence of (1) carbon monoxide, (2) a beryllium, metals belonging to groups IIIA, IVB, VB, VIB of the Periodic Table, lanthanide metals and actinide metals, (3) a rhodium catalyst and (4) an iodine compound, under conditions effective to convert said starting material to acetic acid.

2. A process as claimed in claim 1, in which said metal accelerator is selected from the group consisting of metals belonging to groups IIIA, IVB, and VIB, and beryllium.

3. A process as claimed in claim 1, in which said metal accelerator is selected from the group consisting of aluminum, zirconium, titanium and beryllium.

4. A process as claimed in claim 1, in which said metal accelerator is aluminum.

5. A process as claimed in claim 1, in which said metal accelerator belongs to group IVB.

6. A process as claimed in claim 1, in which the heating step is conducted in the presence of hydrogen gas.

7. A process as claimed in claim 6, in which said metal accelerator is selected from the group consisting of aluminum, zirconium, titanium and beryllium.

8. A process as claimed in claim 6, in which said metal accelerator is beryllium.

9. A process for preparing acetic acid, which comprises:
heating to a temperature of from 100° to 250° C. a liquid starting material selected from the group consisting of
(i) methyl formate,
(ii) a mixture of formic acid and a methyl carboxylate, and
(iii) a mixture of an alkyl formate and a methyl carboxylate, and contacting same with carbon monoxide, in the presence of
from 0.1 to 50 mmol/liter of a rhodium catalyst, from 0.1 to 10 mol/liter of an iodine compound and
from 5 to 700 mmol/liter of a metal accelerator selected from the group consisting of beryllium and metals belonging to groups IIIA, IVB, VB and VIB of the Periodic Table of the elements, lanthanide metals and actinide metals whereby to convert said starting material to acetic acid.

10. A process for preparing acetic acid from a starting material selected from the group consisting of (i) methyl formate and (ii) a mixture of formic acid and a methyl carboxylate, which comprises: heating said starting material in the presence of (1) carbon monoxide, (2) a member selected from the group consisting of organic pentavalent nitrogen onium compounds, trivalent nitrogen precursors thereof, organic pentavalent phosphorus onium compounds, and trivalent phosphorus precursors thereof, and in the presence of chromium, (3) a rhodium catalyst and (4) an iodine compound, under conditions effective to convert said starting material to acetic acid.

11. A process for preparing acetic acid, which comprises: heating to a temperature of from 100° to 250° C. a liquid starting material selected from the group consisting of
(i) methyl formate,
(ii) a mixture of formic acid and a methyl carboxylate, and
(iii) a mixture of an alkyl formate and a methyl carboxylate, and contacting same with carbon monoxide, in the presence of a rhodium catalyst, an iodine compound and an accelerator selected from the group consisting of a metal belonging to groups IIIA, IVB and VIB, and beryllium.

12. A process for preparing acetic acid, which comprises: heating to a temperature of from 100° to 250° C. a liquid starting material selected from the group consisting of
(i) methyl formate,
(ii) a mixture of formic acid and a methyl carboxylate, and
(iii) a mixture of an alkyl formate and a methyl carboxylate, and contacting same with carbon monoxide, in the presence of a rhodium catalyst, an iodine compound and an accelerator selected from the group consisting of aluminum, zirconium, titanium and beryllium.

13. A process for preparing acetic acid, which comprises: heating to a temperature of from 100° to 250° C. a liquid starting material selected from the group consisting of (i) methyl formate,
(ii) a mixture of formic acid and a methyl carboxylate, and
(iii) a mixture of an alkyl formate and a methyl carboxylate, and contacting same with carbon monoxide, in the presence of a rhodium catalyst, an iodine compound and aluminum, as an accelerator.

* * * * *

UNITED STATES PATENT AND TRADEMARK OFFICE
CERTIFICATE OF CORRECTION

PATENT NO. : 4 996 357
DATED : February 26, 1991
INVENTOR(S) : Hidetaka KOJIMA et al It is certified that error appears in the above-identified patent and that said Letters Patent is hereby corrected as shown below:

Column 7, line 60; before "beryllium" insert ---metal accelerator selected from the group consisting of---.

Column 7, line 60; after "VB" change the comma to ---and---.

Signed and Sealed this

Tenth Day of November, 1992

Attest:

DOUGLAS B. COMER

*Attesting Officer*     *Acting Commissioner of Patents and Trademarks*